United States Patent

Bruna et al.

Patent Number: 6,056,169
Date of Patent: May 2, 2000

[54] INHALER APPARATUS FOR DISPENSING ACCURATE AND REPRODUCIBLE DOSES OF POWDER

[75] Inventors: Pascal Bruna, Rouen; Olivier Fourment, Paris, both of France; Guiseppe Stradella, Camogli, Italy

[73] Assignee: Valois S.A., Le Neubourg, France

[21] Appl. No.: 09/029,750

[22] PCT Filed: Aug. 29, 1996

[86] PCT No.: PCT/FR96/01328

§ 371 Date: Jul. 22, 1998

§ 102(e) Date: Jul. 22, 1998

[87] PCT Pub. No.: WO97/09083

PCT Pub. Date: Mar. 13, 1997

[30] Foreign Application Priority Data

Sep. 4, 1995 [FR] France .................................. 95/10354

[51] Int. Cl.⁷ .................................................. A01C 15/04
[52] U.S. Cl. .......................................... 222/636; 604/58
[58] Field of Search ................................ 222/636, 631; 604/58

[56] References Cited

U.S. PATENT DOCUMENTS

| | | | |
|---|---|---|---|
| 5,366,122 | 11/1994 | Guentert et al. | 222/636 |
| 5,383,850 | 1/1995 | Schwab et al. | 222/636 X |
| 5,568,884 | 10/1996 | Bruna | 222/636 X |

FOREIGN PATENT DOCUMENTS

| | | |
|---|---|---|
| 424 790 | 5/1991 | European Pat. Off. . |
| 573 128 | 12/1993 | European Pat. Off. . |
| WO 92/04068 | 3/1992 | WIPO . |
| WO 93/16748 | 9/1993 | WIPO . |
| WO 93/18812 | 9/1993 | WIPO . |

*Primary Examiner*—Gregory L. Huson
*Attorney, Agent, or Firm*—Sughrue, Mion, Zinn, Macpeak & Seas, PLLC

[57] ABSTRACT

An inhaler (1) for dispensing accurate and reproducible doses of powder. The inhaler includes an expulsion channel (2) opening out in an outlet orifice (3), and is characterized by a combination of or: a pre-dosing device (100) having the powder in individual reservoirs (101), each reservoir (101) containing one dose of powder, and; a transfer device (200) for transferring a dose of powder in full into the expulsion channel (2) on each actuation of the inhaler. The inhaler also includes an air flow source (300) having a pump (301) triggerable by the user the air flow source (300) sending a flow of air into the expulsion channel (2) towards the outlet orifice (3) to expel the dose of powder.

7 Claims, 4 Drawing Sheets

INHALER APPARATUS FOR DISPENSING ACCURATE AND REPRODUCIBLE DOSES OF POWDER

The present invention relates to inhaler apparatus, and more particularly to an active dry powder inhaler (DPI) that is also an active breath-actuated inhaler (BAI), i.e. that is triggered by the user inhaling.

The term "active DPI" is used to mean a powder dispenser in which the dose of powder is dispensed by means of a flow of air propelled independently from the user inhaling. Such devices are mainly used for dispensing powders, in particular medicines, that are intended to be dispensed to the user in an accurately-measured manner, at a moment that is accurately determined, and also to a location that is accurately determined, specifically the lungs. This applies in particular to certain medicines for suffers of asthma where it is desirable for as reproducible as possible a quantity of powder to reach as deeply as possible into the lungs of the patient. For this purpose, it is essential that the dose of powder expelled by the inhaler is determined accurately and reproducibly, for the doses of powder always to be expelled under the same conditions, and for said expulsions to be coordinated with the patient inhaling (active BAI).

Such an inhaler is described in particular in document WO 93/18812. That document discloses an inhaler having a powder reservoir and measuring means that make it possible on each actuation of the inhaler to fill a measuring chamber with a dose of powder, the inhaler also including a source of compressed air that is triggerable by inhaling and that establishes a flow of compressed air that expels the dose of powder situated in the measuring chamber.

Depending on the type of powder or medicine used, and depending on the use for which the inhaler is intended, the inhaler disclosed in document WO 93/18812 can suffer from various drawbacks. Thus, packaging all of the powder in a single reservoir means that in the event of a portion of said powder becoming contaminated and/or moist, then all of the powder is in danger of becoming contaminated and/or moist. Also, for powders including fragile molecules, e.g. molecules made up of long chains, there is a danger of the molecules being broken during the dosing operation, and that can spoil the effectiveness of the powder. In addition, the reservoir may include certain amounts of dead space, and the powder contained in the dead space can fail to be transferred into the measuring chamber by the dosing means, and that constitutes a drawback when the powder in question is very expensive. In addition, dose reproducibility is not good.

Document WO 93/16748 discloses an inhaler including a device for transferring doses of powder from a common reservoir. That device improves dose reproducibility, but continues to suffer from the other above-mentioned drawbacks.

Document WO 94/08552 discloses an inhaler having a pre-dosing device in the form of individual powder reservoirs, the inhaler further including an electric motor that is triggered by the user inhaling, said electric motor propelling a flow of air for expelling a dose when the patient inhales. That inhaler suffers from a major drawback in that it includes electrical means for dispensing the dose, thereby considerably increasing its cost, making it difficult to manufacture, and making it dependent on a supply of electricity to operate.

An object of the present invention is to provide an inhaler that avoids the above-mentioned drawbacks and that operates in optimum manner. To operate in optimum manner, such an inhaler must simultaneously satisfy each of the following conditions in optimal manner:

all of the powder contained in the inhaler must be protected from any external contamination and/or moistening;

all of the powder contained in the inhaler must be dispensed in doses that are very accurately reproducible;

each dose must be expelled in a manner that is coordinated with the patient inhaling; and each dose of powder must penetrate in finely divided form deep into the lungs of the user.

The present invention also seeks to provide an inhaler capable of dispensing all of the powder contained in the inhaler in a manner that is accurate and economical, while avoiding any chance of the powder being spoiled in any way whatsoever.

The present invention thus provides an inhaler for dispensing accurate and reproducible doses of powder, said inhaler including an expulsion channel opening out in an outlet orifice, and being characterized in that it comprises in combination:

a pre-dosing device having the powder in individual reservoirs, each reservoir containing one dose of powder;

a transfer device for transferring a dose of powder in full into the expulsion channel on each actuation of the inhaler; and an air flow source comprising a pump triggerable by the user inhaling, the air flow source sending a flow of air into channel towards the outlet orifice to expel the dose of powder.

Thus, it is the combination of the above-specified technical means that makes it possible to solve the technical problem of the invention: the pre-dosing device using individual reservoirs makes it possible to avoid any risk of the entire supply of powder being contaminated and/or moistened. Even if the powder contained in one of the reservoirs should be contaminated and/or moistened, the rest of the powder is unaffected. In addition, the pre-dosing device guarantees good dose reproducibility since each reservoir contains exactly one dose, with the entire dose being transferred for expulsion purposes by means of the transfer device. Thereafter, the source of air flow enables a highly reproducible flow of air to be established that is suitable for expelling the various doses of powder under the same conditions. Similarly, this flow of air makes it possible, where necessary, to break up any agglomeration in the dose of powder prior to expulsion thereof, thus guaranteeing that the powder is in finely divided form, thereby enhancing its penetration into the lungs. This is further amplified by the expulsion of the dose being coordinated with the user inhaling.

In particular, the pump is prestressed and includes a piston sliding in a chamber connected to the expulsion channel, the piston being biased by a spring, the spring being manually compressible, and the piston being held against the force exerted by the compressed spring by a locking member, the locking member being released by the user inhaling so that the spring relaxes and thereby displaces the piston in the chamber, thereby establishing a flow of air through the expulsion channel.

Advantageously, the pre-dosing device comprises a support provided with at least one reservoir, each reservoir containing an accurate dose of powder, the transfer device including means for driving the support to bring one of the reservoirs into the expulsion channel prior to the user inhaling.

Advantageously, the reservoirs are hermetically sealed from the atmosphere, the transfer device including opening and transfer means for opening the reservoir and transferring its dose of powder into the expulsion channel before the user inhales.

Other advantages and characteristics of the invention appear from the following detailed description given by way of non-limiting example and made with reference to the accompanying drawings, in which.

Figure 3A:
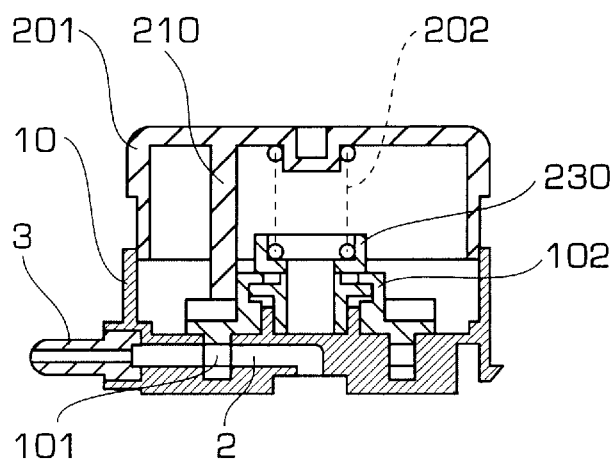
FIGS. 3a and 3b are diagrammatic section views through a particular embodiment of devices for pre-dosing and transferring powder in an inhaler of the invention, shown respectively in a ready position and in a position in which the transfer device is actuated.
Figure 3B:
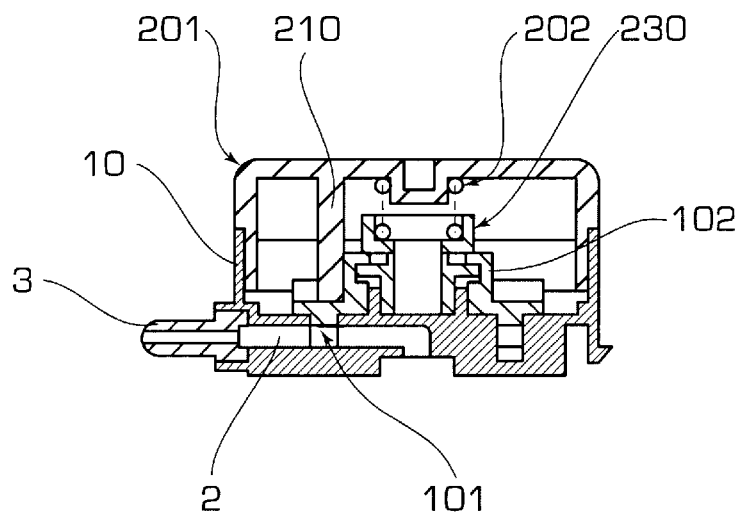
Figure 3C:
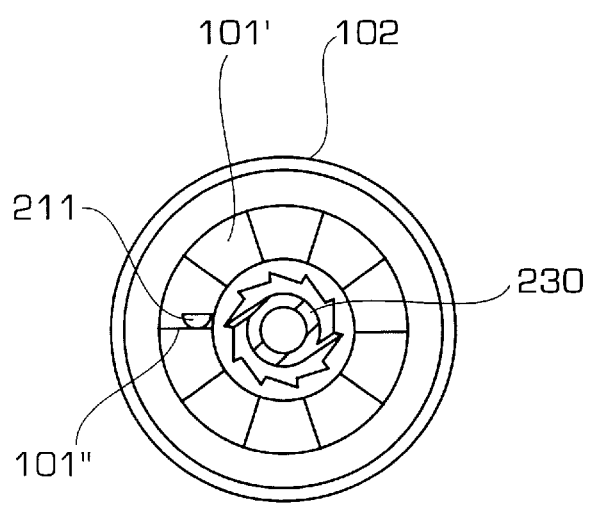
FIG. 3c is a plan view of the pre-dosing device of FIGS. 3a and 3b.
Figure 3D:
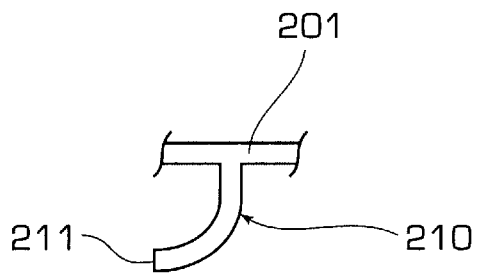
Figure 4A:
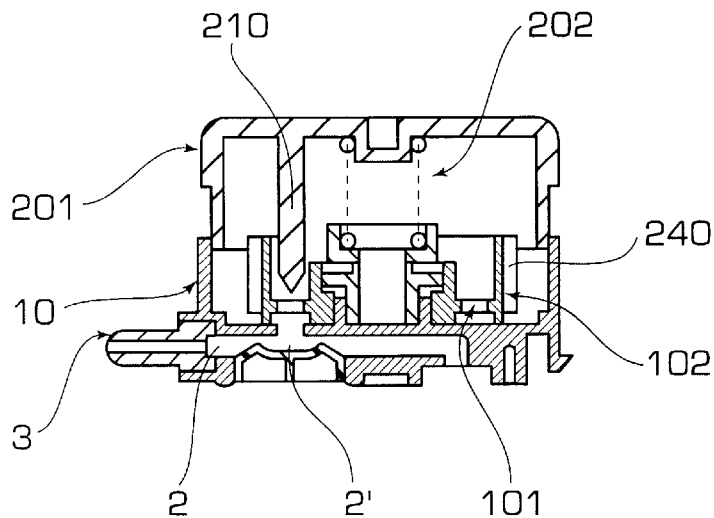
Figure 4B:
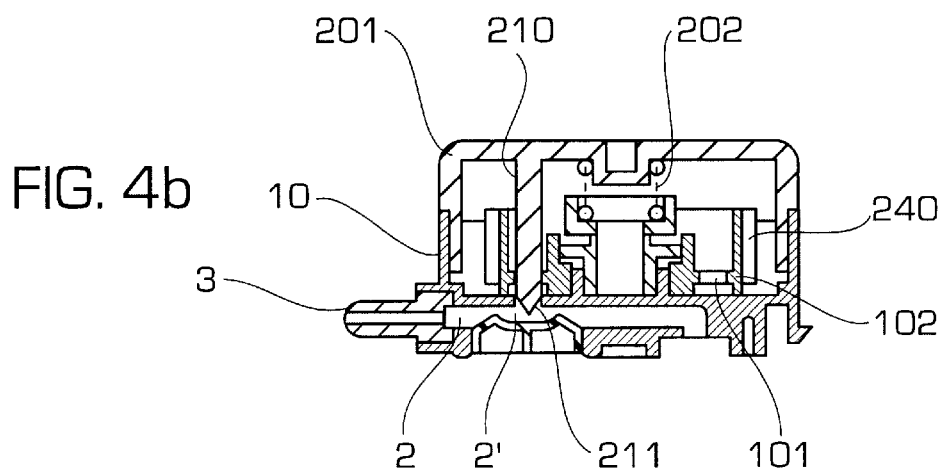
Figure 4C:
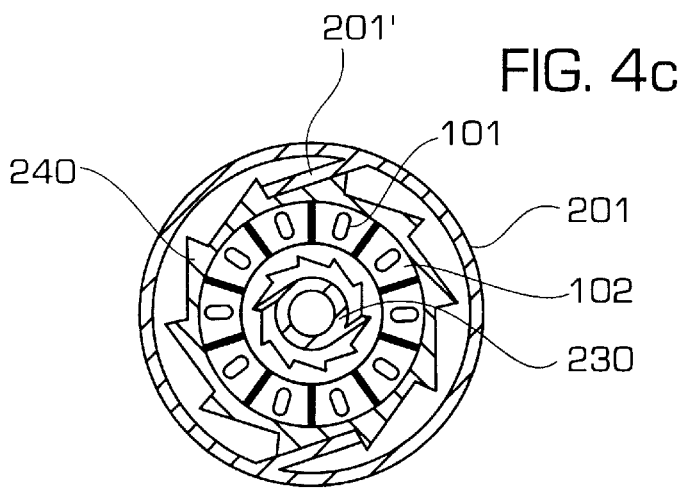

FIG. 3d is a side view of a portion of the transfer device of FIGS. 3a and 3b; and FIGS. 4a, 4b, and 4c are views similar to those of FIGS. 3a, 3b, and 3c, respectively, showing another embodiment of the pre-dosing device and the transfer device of the invention.

Figure 1:
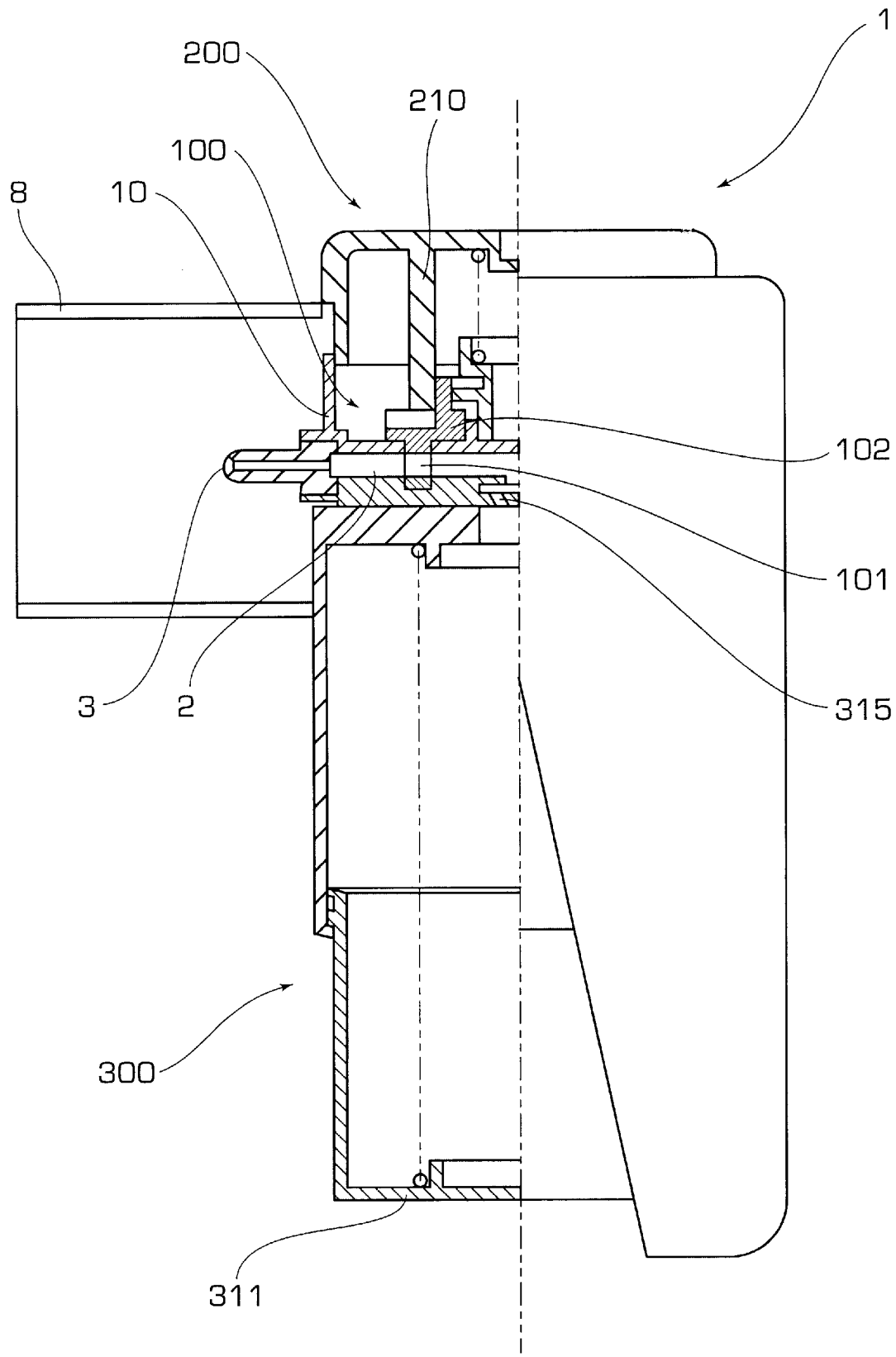
FIG. 1 is a diagrammatic section view of an inhaler constituting a particular embodiment of the invention.

With reference to FIG. 1, there can be seen a diagram of an inhaler constituting a particular embodiment of the invention. The inhaler 1 comprises an air flow source 300, shown in greater detail in FIG. 2, together with a pre-dosing device 100 and a transfer device 200, with two different embodiments thereof being shown in FIGS. 3a to 3d and in FIGS. 4a to 4c, respectively.

The inhaler 1 has an expulsion channel 2 which extends at one end towards an outlet orifice 3 which is advantageously located in a mouthpiece 8, and is connected at its other end to the air flow source 300.

The air flow source 300 comprises a pump 301, preferably a prestressed pump that is triggered by the user inhaling. An example of such an air flow source is disclosed in document WO 93/18812, and its operation and implementation are consequently outlined only briefly with reference to FIG. 2, it being understood that all of the variants disclosed in document WO 93/18812 are equally applicable in this case. Similarly, it is clear that other known air flow source devices could also be used in this application, providing they include a pump enabling a flow of air to be propelled through the expulsion channel of the inhaler, with said flow of air being triggered by the user inhaling.

Figure 2:
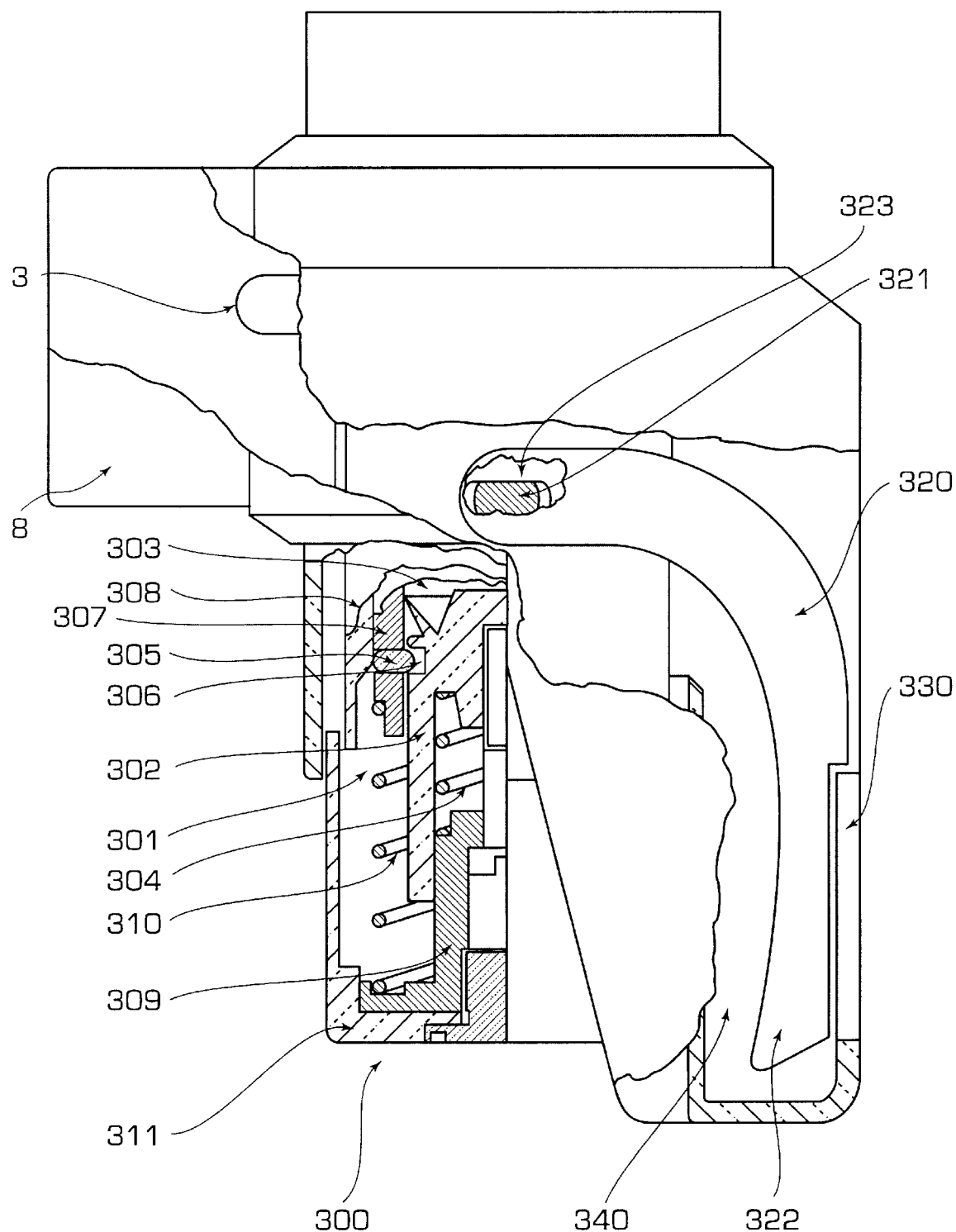
FIG. 2 is a diagrammatic section view through a particular embodiment of the air flow source for an inhaler of the invention.

With reference to FIG. 2, one example of such an air flow source 300 is shown diagrammatically. The air flow source 300 comprises a pump 301 which is manually prestressed. The pump 301 has a piston 302 which slides in a chamber 303 between a rest position and an actuated position, said chamber 303 being connected to the expulsion channel 2 of the inhaler, e.g. via an outlet check valve 315 from the chamber 303. The piston 302 is urged towards its actuated position by a spring 304 which can be compressed manually by means of a compression member 309 secured to the bottom 311 of the inhaler. While the spring 304 is being compressed, the piston 302 is held in its rest position by a locking member 305, specifically a split ring 305 received in the body 307 forming the chamber 303 and held in a groove 306 of the piston by means of a sliding sleeve 308 which prevents said split ring 305 from escaping from said groove 306 of the piston 302. Thus, the user cocks the pump by compressing the spring 304 via the compression member 309 by pressing on the bottom 311 of the inhaler. In order to be coordinated with the patient inhaling, the air flow source includes a lever type element 320 which, in the rest state, has an end 322 covering and closing an opening 330 formed through the body of the inhaler. The lever 320 can pivot about its connection point 321, said connection point being situated in the vicinity of an element 323 secured to said above-mentioned sliding sleeve 308. Thus, when the user inhales through the mouthpiece 8, suction is established in the space 340 situated facing the opening 330 of the inhaler body, thereby causing the lever 320 to pivot inwards about its connection point 321, and in turn acting on the element 323 secured to the sleeve 308 by displacing it slightly upwards. Upward displacement of the sleeve 308 releases the split ring 305 which, under the effect of the force exerted by the spring 304 on said piston 302, is forced outwards from the groove 306 of the piston 302 so that the piston 302 is no longer retained by the locking member and can slide inside the chamber 303 under drive from the spring 304. The piston 302 thus expels the air contained inside the chamber 303 via the outlet valve 315 from said chamber into the expulsion channel 2 to expel the dose of powder, said expulsion being triggered by the user inhaling.

With reference to FIGS. 3a to 3d, and to FIGS. 4a to 4d, there are shown two different embodiments of the pre-dosing device and of the transfer device for the inhaler of the invention.

To avoid all of the powder becoming contaminated and/or moistened in the event of a portion of the powder being contaminated and/or moistened, and in order to guarantee good reproducibility of the dose of powder and to avoid any loss of powder in any dead volume of a single reservoir, the invention provides for using a pre-dosing device made up of individual reservoirs. In the example shown in FIGS. 3a to 3d, the pre-dosing device 100 comprises a plurality of individual reservoirs 101, and in this case ten reservoirs. These individual reservoirs 101 are provided in a support, specifically a rigid disk 102, which is rotatable inside the top body 10 of the inhaler, through which the expulsion channel 2 is formed. Each reservoir 101 has an inlet orifice and an outlet orifice suitable for being brought into alignment with said expulsion channel 2, such that when a reservoir 101 is disposed in said expulsion channel 2, the powder contained therein can be expelled by the flow of air propelled by the above-described air flow source 300. Advantageously, the disk 102 containing the reservoirs 101 rotates inside the inhaler body 10 in sealed manner and gaskets (not shown) may be provided about junctions between the inlet and outlet orifices of the reservoir and the expulsion channel, whenever a said reservoir is located in said expulsion channel. These gaskets may serve to guarantee sealing while the dose is being expelled by the flow of air.

The transfer device 200 that is designed to replace one of the reservoirs 101 in said expulsion channel 2 prior to each use of the inhaler comprises a pushbutton 201 that is movable axially relative to the body 10 of the inhaler between a rest position and an actuated position. The pushbutton is urged towards its rest position by a spring 202. As shown in FIGS. 3a, 3b, 3c, and 3d, the transfer device 200 also includes a finger 210 whose end 211 is flexible and capable of curving when the pushbutton 201 is moved from its rest position (FIG. 3a) to its actuated position (FIG. 3b). The end 211 of said finger 210 co-operates with a housing 101' corresponding to each individual reservoir 101 of the pre-dosing device. As shown in FIG. 3c, the end 211 of the finger 210 comes into abutment against a wall 101" of said housing 101' which is secured to each reservoir 101, and continued axial displacement of the pushbutton 201 towards its actuated position as shown in FIG. 3b causes said pre-dosing device 100 to rotate, thereby bringing the next reservoir 101 into the expulsion channel 2 of the inhaler. To prevent rotation in the opposite direction, an antireturn pawl 230 can advantageously be disposed inside the rigid disk 102 of the pre-dosing device. By way of example, said antireturn pawl 230 may co-operate with circumferential teeth on the disk, as shown in FIG. 3c. When the pushbutton 201 is in the actuated position as shown in FIG. 3b, a reservoir 101 lies in the expulsion channel 2 of the inhaler, and the spring 202 then returns the pushbutton 201 to its rest position as shown in FIG. 3a. The user then need only cock the air flow source and inhale, thereby triggering said flow of air which expels the dose of powder contained in said reservoir 101 and sends it through the orifice 3 towards the user.

With reference to FIGS. 4a, 4b, and 4c, another embodiment of the pre-dosing device and of the transfer device is shown. In this example, the pre-dosing device is disposed above the expulsion channel 2, and a measuring chamber 2' can be provided in said channel 2 to receive a dose of powder that is to be expelled. In this way, the pre-dosing device 100 also includes a rigid disk acting as a support 102, said disk including a plurality of reservoirs 101 each implemented in the form of a through hole passing through said disk 102, and disposed around the circumference thereof. Each reservoir 101, i.e. each opening, is closed on two sides by an impermeable layer such that each reservoir 101 is hermetically closed from the atmosphere and the doses of powder contained in the reservoirs 101 are prevented from being contaminated and/or moistened. The transfer device 200 also includes a pushbutton 201 which, unlike the pushbutton of the first embodiment described above, is movable both axially and in rotation relative to the inhaler. Thus, to place a reservoir 101 in register with the measuring chamber 2' disposed in the expulsion channel 2 of the inhaler, the pushbutton 202 is turned, e.g. clockwise (FIG. 4c). The pushbutton 201 has one or more tongues 201' that co-operate advantageously with a set of teeth 240 secured to the support 102 of said reservoirs 101, such that said rotation causes said support to turn, thereby moving a reservoir 101 into register with said measuring chamber 2' of the inhaler. Thereafter, the pushbutton 201 is turned in the opposite direction to be returned to its initial position. During this operation, an antireturn pawl 230 is advantageously provided secured to the body 10 of the inhaler and co-operating with an internal set of teeth secured to the disk 102, for example, to prevent the disk from moving while the pushbutton 201 is being returned to its initial position. The pushbutton 201 also includes a finger 210 located in register with both the measuring chamber 2' and a reservoir 101 once the pushbutton 201 is in its initial position. The finger 210 is advantageously provided with an end 211 adapted to piercing the closure layers of each reservoir 101 so that when pressure is applied to said pushbutton 201 it moves axially from its position shown in FIG. 4a towards its position shown in FIG. 4b, with the end 211 of the finger 210 passing through both closure walls and transferring the dose of powder into the measuring chamber 2' lying in the expulsion channel 2 of the inhaler. In this way, inhaling triggers the above-described air flow source 300 and sends a flow of air through the expulsion channel 2, thereby emptying the dose of powder from the measuring chamber 2'. The spring 202 then returns the pushbutton 201 towards its rest position of FIG. 4a.

Naturally, the above description of various devices forming the combination of the invention, namely the pre-dosing device, the transfer device, and the air flow source, can vary in any known manner and the examples described are not limiting. The essential point of the invention lies in the fact that each of said devices operates in optimum manner to provide an inhaler that is triggered by inhaling and that is as effective as possible. Thus, a pre-dosing device comprising a flexible strip as its support instead of a rigid disk is applicable to the present invention. Under such circumstances, the corresponding transfer device serves to drive the strip and open its reservoirs to transfer respective doses of powder into the expulsion channel of the inhaler prior to inhaling on each occasion.

We claim:

1. An inhaler (1) for dispensing accurate and reproducible doses of powder, said inhaler including an expulsion channel (2) opening out in an outlet orifice (3), and being characterized in that it comprises in combination:

a pre-dosing device (100) having the powder in individual reservoirs (101), each reservoir (101) containing one dose of powder;

a transfer device (200) for transferring a dose of powder in full into said expulsion channel (2) on each actuation of the inhaler; and an air flow source (300) comprising a pump (301) triggerable by the user inhaling, said air flow source (300) sending a flow of air into said expulsion channel (2) towards said outlet orifice (3) to expel said dose of powder;

wherein said reservoirs (101) are hermetically sealed from the atmosphere;

and wherein said transfer device (200) includes opening means and transfer means for respectively opening the reservoir (101) and transferring its dose of powder into said expulsion channel (2) before the user inhales.

2. An inhaler according to claim 1, in which said pump (301) is prestressed and includes a piston (302) sliding in a chamber (303) connected to said expulsion channel (2), said piston (302) being biased by a spring (304), said spring (304) being manually compressible, and said piston (302) being held against the force exerted by said compressed spring (304) by a locking member (305), said locking member (305) being released by the user inhaling so that the spring (304) relaxes and thereby displaces said piston (302) in said chamber (303), thereby establishing a flow of air through said expulsion channel (2).

3. An inhaler according to claim 1, in which said pre-dosing device (100) comprises a support (102) provided with at least one reservoir (101), each reservoir (101) containing an accurate dose of powder, the transfer device (200) including means for driving said support (102) to bring one of said reservoirs (101) into the expulsion channel (2) prior to the user inhaling.

4. An inhaler according to claim 2, in which said pre-dosing device (100) comprises a support (102) provided with at least one reservoir (101), each reservoir (101)

containing an accurate dose of powder, the transfer device (200) including means for driving said support (102) to bring one of said reservoirs (101) into the expulsion channel (2) prior to the user inhaling.

5. An inhaler according to claim 1, in which the reservoirs (101) are hermetically sealed from the atmosphere, said transfer device (200) including opening and transfer means for opening the reservoir (101) and transferring its dose of powder into the expulsion channel (2) before the user inhales.

6. An inhaler according to claim 3, in which the reservoirs (101) are hermetically sealed from the atmosphere, said transfer device (200) including opening and transfer means for opening the reservoir (101) and transferring its dose of powder into the expulsion channel (2) before the user inhales.

7. An inhaler according to claim 4, in which the reservoirs (101) are hermetically sealed from the atmosphere, said transfer device (200) including opening and transfer means for opening the reservoir (101) and transferring its dose of powder into the expulsion channel (2) before the user inhales.

* * * * *